United States Patent
Shekalim et al.

(10) Patent No.: US 11,191,655 B2
(45) Date of Patent: Dec. 7, 2021

(54) EXPANDING STENT

(71) Applicant: BioSert Ltd., Nesher (IL)

(72) Inventors: Avraham Shekalim, Nesher (IL); Noam Peleg, Gan Ner (IL)

(73) Assignee: BIOSERT LTD., Nesher (IL)

( * ) Notice: Subject to any disclaimer, the term of this patent is extended or adjusted under 35 U.S.C. 154(b) by 27 days.

(21) Appl. No.: 16/527,114

(22) Filed: Jul. 31, 2019

(65) Prior Publication Data

US 2020/0138608 A1 May 7, 2020

Related U.S. Application Data

(60) Provisional application No. 62/827,897, filed on Apr. 2, 2019, provisional application No. 62/755,498, filed on Nov. 4, 2018.

(51) Int. Cl.
| | |
|---|---|
| *A61F 2/88* | (2006.01) |
| *A61F 2/92* | (2013.01) |
| *A61F 2/07* | (2013.01) |
| *A61F 2/95* | (2013.01) |

(52) U.S. Cl.
CPC .................. *A61F 2/88* (2013.01); *A61F 2/07* (2013.01); *A61F 2/92* (2013.01); *A61F 2/95* (2013.01); *A61F 2210/0004* (2013.01); *A61F 2230/0069* (2013.01); *A61F 2230/0091* (2013.01)

(58) Field of Classification Search
CPC .................................. A61F 2/852; A61F 2/93
See application file for complete search history.

(56) References Cited

U.S. PATENT DOCUMENTS

| | | | |
|---|---|---|---|
| 2005/0165470 A1* | 7/2005 | Weber | A61F 2/88 623/1.15 |
| 2010/0292776 A1* | 11/2010 | Weber | A61F 2/91 623/1.15 |
| 2016/0302911 A1* | 10/2016 | Soletti | A61L 27/18 |
| 2017/0181872 A1* | 6/2017 | Kwon | A61L 27/58 |

* cited by examiner

*Primary Examiner* — Yashita Sharma
(74) *Attorney, Agent, or Firm* — Mark M. Friedman (57) ABSTRACT

A compound stent device includes a first stent portion and a second stent portion, where the second stent portion is formed from a biodegradable material, and the first stent portion is formed from either non-biodegradable material or is biodegradable significantly more slowly than the second portion. The compound stent device is deformable from a first diameter to a second larger diameter. Immediately after expansion, the first stent portion and the second stent portion cooperate to provide a first contact area of support for a length of a surrounding vessel. After decomposition of the second stent portion, the first stent portion provides a second contact area of support for the length of the surrounding vessel which is at least 10 percent smaller than the first contact area.

14 Claims, 13 Drawing Sheets

DETAIL V1

DETAIL XI

EXPANDING STENT

FIELD AND BACKGROUND OF THE INVENTION

The present invention relates to expanding stents and, in particular, it concerns an expanding stent with timed partial degradation and/or particular structural characteristics.

Stents are widely used in conjunction with balloon angioplasty to keep open a blood vessel after deflation of the balloon. Permanent metal stents remain permanently within the blood vessel.

Bioresorbable or bioabsorbable stents (referred to generically as biodegradable stents or degradable stents) undergo a process through which they break down over time and disappear, either being absorbed into or eliminated from the body. Such stents promise various potential advantages, but pose challenges in finding appropriate combinations of longevity until degradation and mechanical strength, and are limited by the impairment of mechanical properties which occurs progressively during the degradation process from the time of insertion onwards.

SUMMARY OF THE INVENTION

The present invention is an expanding stent with timed partial degradation and/or particular structural characteristics.

According to the teachings of an embodiment of the present invention there is provided, a compound stent device comprising: (a) a first stent portion; and (b) a second stent portion formed from a biodegradable material, wherein the compound stent device is deformable from an initial compact state having a generally cylindrical profile with a first external diameter to an expanded state having a second external diameter greater than the first external diameter by a factor of at least two, wherein, in the expanded state immediately after expansion, the first stent portion and the second stent portion cooperate to provide a first contact area of support for a length of a surrounding vessel, and wherein, in the expanded state after decomposition of the second stent portion, the first stent portion provides a second contact area of support for the length of the surrounding vessel, the second contact area being smaller than the first contact area by at least about 10 percent.

According to a further feature of an embodiment of the present invention, the second contact area is smaller than the first contact area by at least about 40 percent.

According to a further feature of an embodiment of the present invention: (a) in the expanded state immediately after expansion, the first stent portion and the second stent portion cooperate to provide support for a length of a surrounding vessel around an entire internal periphery of the vessel, and (b) in the expanded state after decomposition of the second stent portion, the first stent portion remains supporting more than half of the periphery of the vessel while leaving a continuous swath of at least 30 degrees of the periphery of the vessel free from contact with the stent device.

According to a further feature of an embodiment of the present invention, the first stent portion is formed from a non-biodegradable material.

According to a further feature of an embodiment of the present invention, the first stent portion is formed from a biodegradable material that decomposes more slowly within the body than the biodegradable material of the second stent portion.

According to a further feature of an embodiment of the present invention, the first stent portion is formed from the same biodegradable material as the second stent portion, and wherein the first stent portion is formed with a thicker structure than the second stent portion so that the first stent portion decomposes more slowly within the body than the second stent portion.

According to a further feature of an embodiment of the present invention, the first stent portion is formed from a biodegradable material and is configured to decompose over a first time period, and wherein the second stent portion is configured to decompose over a second time period, the first time period being at least 2 months longer than the second time period.

According to a further feature of an embodiment of the present invention, the second time period is between 1 week and 3 months.

According to a further feature of an embodiment of the present invention, each of the first and second stent portions is formed with a backbone extending along a length of the stent portion and a plurality of struts projecting from each side of the backbone.

According to a further feature of an embodiment of the present invention, the second stent portion is deployed with its backbone in opposing relation to the backbone of the first stent portion.

According to a further feature of an embodiment of the present invention, the first stent portion is formed primarily from stainless steel.

According to a further feature of an embodiment of the present invention, the second stent portion is formed primarily from magnesium.

According to a further feature of an embodiment of the present invention, the second stent portion is configured to decompose within a blood vessel over a period of less than 3 months.

There is also provided according to the teachings of an embodiment of the present invention, a compound stent device comprising: (a) a first stent portion formed from a non-biodegradable material; and (b) a second stent portion formed from a biodegradable material, wherein the compound stent device is deformable from an initial compact state having a generally cylindrical profile with a first external diameter to an expanded state having a second external diameter greater than the first external diameter by a factor of at least two, wherein, in the expanded state immediately after expansion, the first stent portion and the second stent portion cooperate to provide a first contact area of support for a length of a surrounding vessel, and wherein, in the expanded state after decomposition of the second stent portion, the first stent portion provides a second contact area of support for the length of the surrounding vessel, the second contact area being smaller than the first contact area by at least about 10 percent.

According to a further feature of an embodiment of the present invention, the second contact area is smaller than the first contact area by at least about 40 percent.

According to a further feature of an embodiment of the present invention: (a) in the expanded state immediately after expansion, the first stent portion and the second stent portion cooperate to provide support for a length of a surrounding vessel around an entire internal periphery of the vessel, and (b) in the expanded state after decomposition of the second stent portion, the first stent portion remains supporting more than half of the periphery of the vessel while leaving a continuous swath of at least 30 degrees of the periphery of the vessel free from contact with the stent device.

There is also provided according to the teachings of an embodiment of the present invention, compound stent device comprising: (a) a first stent portion formed from a non-biodegradable material; and (b) a second stent portion formed from a biodegradable material, wherein the compound stent device is deformable from an initial compact state having a generally cylindrical profile with a first external diameter to an expanded state having a second external diameter greater than the first external diameter by a factor of at least two, wherein, in the expanded state immediately after expansion, the first stent portion and the second stent portion cooperate to provide support for a length of a surrounding vessel around an entire internal periphery of the vessel, and wherein, in the expanded state after decomposition of the second stent portion, the first stent portion remains supporting more than half of the periphery of the vessel while leaving a continuous swath of at least 30 degrees of the periphery of the vessel free from contact with the stent device.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an expanding stent with timed partial degradation.

The principles and operation of stents according to the present invention may be better understood with reference to the drawings and the accompanying description.

The following detailed description is of the best currently contemplated modes of carrying out the invention. The description is not to be taken in a limiting sense, but is made merely for the purpose of illustrating the general principles of the invention, since the scope of the invention is best defined by the appended claims. In particular, although reference may be made to coronary stents and to angioplasty, such references are merely by way of non-limiting exemplary applications, but should not be considered to limit the present invention to such applications.

Figure 1:
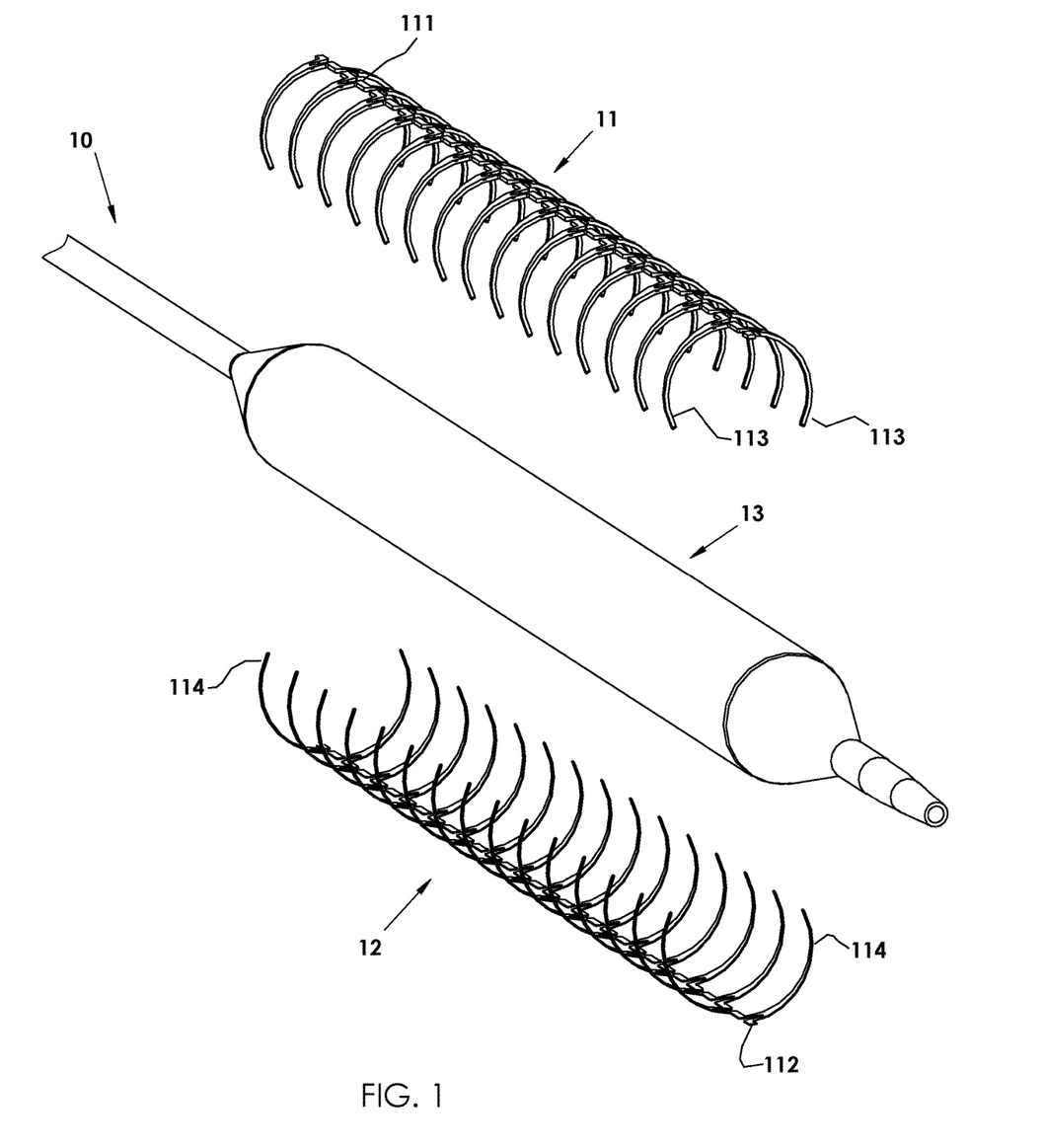
FIG. 1 is an isometric exploded view of a stent kit, constructed and operative according to the teachings of an embodiment of the present invention, including two parts of a compound stent and a deployment balloon.
Figure 2:
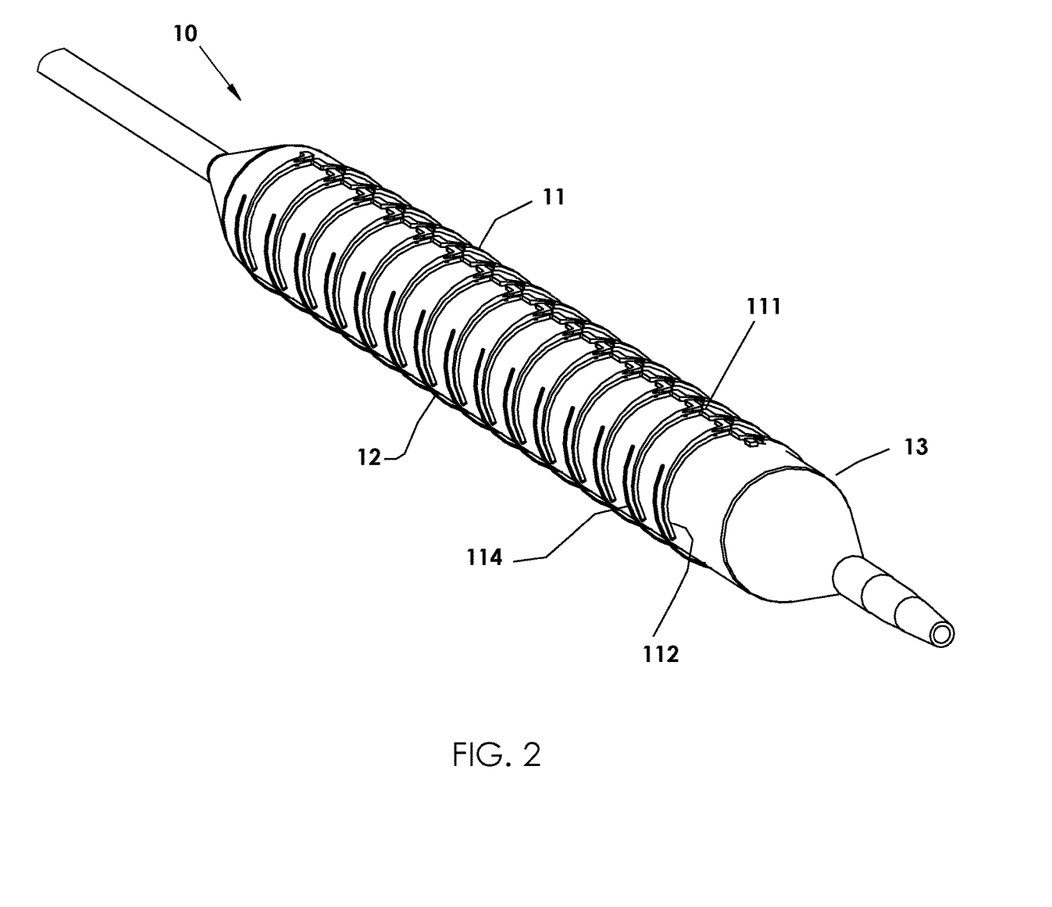
FIG. 2 is an isometric view of the stent kit of FIG. 1 assembled, illustrating the state of the kit after full inflation of the deployment balloon.

According to a first aspect of the present invention, there is provided a compound stent for an artery that reduces risks of restenosis. In accordance with FIG. 1, the compound stent device (10) includes a first stent portion, implemented as a non-biodegradable stent (11), and a second stent portion, implemented as a biodegradable stent (12), which is combined for use with an angioplasty balloon (13) to form a "stent kit". In alternative implementations, stent (11) may be formed also from biodegradable material, but where the material and/or structure of stent (11) are chosen to provide a sufficiently slow rate of degradation that stent (11) remains structurally intact after stent (12) has disappeared, all as detailed further below. In accordance to FIG. 2 the stents (11 and 12) are mounted opposite to each other (i.e., with their backbones in opposing relation, as described further below) on the angioplasty balloon (13), shown here in a deployed (expanded) state in which the angioplasty balloon has expanded the stents to a final expanded state. The two stents together cover the whole perimeter of the balloon to support the whole perimeter of the blood vessel. In their deployed state, each stent individually typically extends around less than the entire periphery of the inner wall of the vessel, typically leaving between 30 to 170 degrees of the perimeter open, but that open area is supported by the other stent.

Thus, each stent can be opened peripherally within an artery from a closed position (FIG. 4) to an open position (FIG. 2) such that in the open position a periphery of the stent has a longitudinal opening spanning a length of the stent. Each stent is preferably configured so as not to scrape or penetrate the blood vessel wall when it opens peripherally. Instead, the peripheral surface of the stent preferably slides along an interior blood vessel wall in a direction of expansion of the blood vessel wall without leading edges of the peripheral surface contacting the interior blood vessel wall. The peripheral surface, which may have a "backbone" (111 and 112, respectively) and arcuate branches or "ribs" (113 and 114, respectively), which are curved and, when the stent opens peripherally in the blood vessel, the surfaces of the peripheral ribs contact the interior blood vessel wall in a non-lacerating sliding motion. Certain examples of stent structures which are suitable for implementing one or both of stents (11) and (12) are described in coassigned U.S. Pat. No. 9,980,836. Details of the structure and function of certain preferred implementations of the stents described herein should be understood to be according to the description of the stents in the aforementioned patent except where stated herein otherwise. It should be noted however that the principles of the present invention are not limited to this type of stent, and can also be implemented in the context of various other conventional stent configurations.

The term "biodegradable" (or "degradable") is used herein generically to refer to any material which, over a period of time, undergoes a process which gradually removes the material so that the structure eventually disappears without further intervention. The term thus defined includes any and all materials which undergo such a process, whether the process is a physical process, a biological process or a chemical process, and whether the material is eliminated from the body or otherwise used or absorbed by the body, and encompasses materials referred to a bioresorbable, bioabsorbable, and all other forms of gradual decomposition within the body. The term "non-biodegradable" is used herein generically to refer to any implant material which remains indefinitely as a structural material within the body.

The non-biodegradable stent (11) is preferably made of high strength bio-inert material such as (but not limited to) stainless steel 316 for example. The biodegradable stent is preferably made of magnesium or a magnesium alloy. Alternatively, it may be made of bio-degradable polymer such as poly-L-lactic acid (PLLA), polyglycolic acid (PGA), poly (D,L-lactide/glycolide) copolymer (PDLA), and polycaprolactone (PCL). Alternatively, other metallic alloys utilized for bioabsorbable stents such as iron may be used. The above materials are to serve only as examples for relevant biodegradable materials and the invention is not limited to those examples.

As known in the art, the biodegradable stent may advantageously be used as a delivery vehicle for anti-inflammatory drugs and/or other medications or substances with therapeutic effects. The medications may be carried within the bulk of the biodegradable stent or may be included in coatings applied to the stent. The biodegradable stent essentially serves to ensure that no flap of tissue ingresses into the vessel through the open swath of the non-biodegradable stent during and immediately after the deployment and expansion procedure, and/or to provide delivery of therapeutic agents. In certain cases, a relatively lesser structural strength and rigidity is required for the biodegradable stent compared to a stand-alone stent which must independently support the vessel wall. This in some cases allows choice of a relatively thin stent material, in some cases thinner than the biodegradable stent, where the thickness of the biodegradable stent is chosen primarily according to the desired period of support in relation to the rate of break-down of the stent material. In some cases, the angular extent of the biodegradable stent and/or the number of ribs extending therefrom may be different from (typically less than) the corresponding parameters of the non-biodegradable stent. Typically, the angular extent of the biodegradable stent is chosen to be similar to that of the non-biodegradable stent, so that the maximum degree of radial extension which can be obtained is the same for both stents while maintaining spanning of more than 180 degrees by each stent individually, and preferably ensuring coverage of a full 360 degrees between the two stents combined, as discussed further below.

Figure 3A:
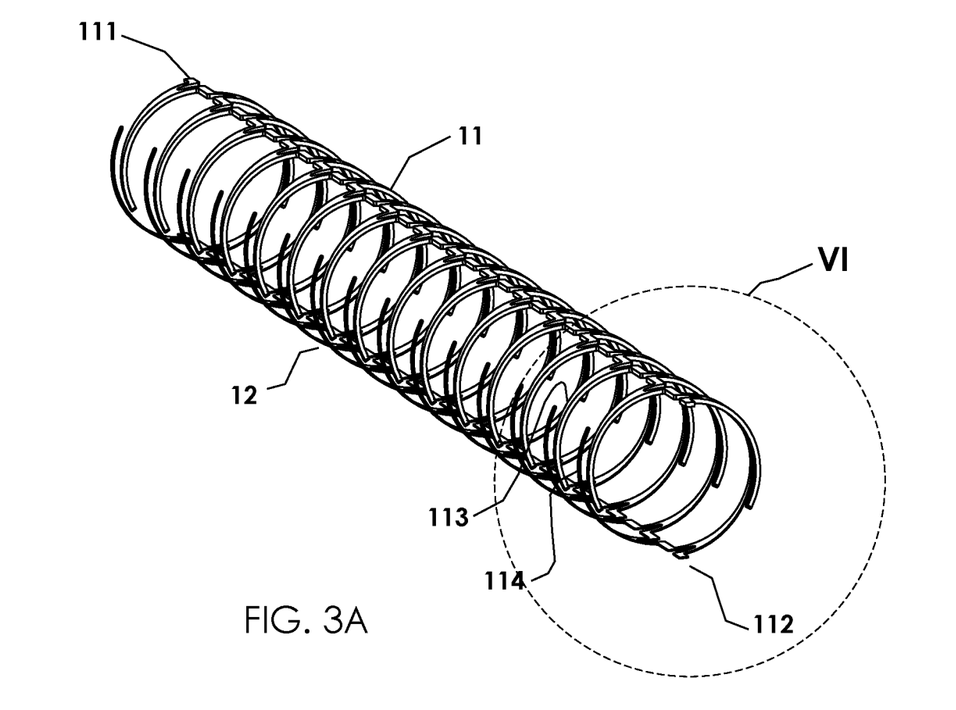
FIG. 3A is an isometric view illustrating the configuration of the compound stent immediately after deflation and removal of the deployment balloon.

As illustrated in FIG. 3A, right after the deflation of the balloon, the stents support the whole perimeter (360 degrees) of the vessel. The degradation process of the degradable stent (12) begins at the time of implantation. The degradation process preferably takes a few weeks. During this time the vessel wall is healed from the trauma caused by the angioplasty process.

In certain particularly preferred implementations, a majority of the mechanical support to prevent recoiling of the vessel is generally achieved by the non-degradable stent while the degradable stent serves primarily to prevent ingress of residual tissue flaps through the open part of the non-degradable stent. Hence, the struts of the degradable stent can be implemented as the minimum required to provide the support necessary for this task. The use of thin struts typically causes lesser injury and improves integration into the vessel wall.

Figure 3B:
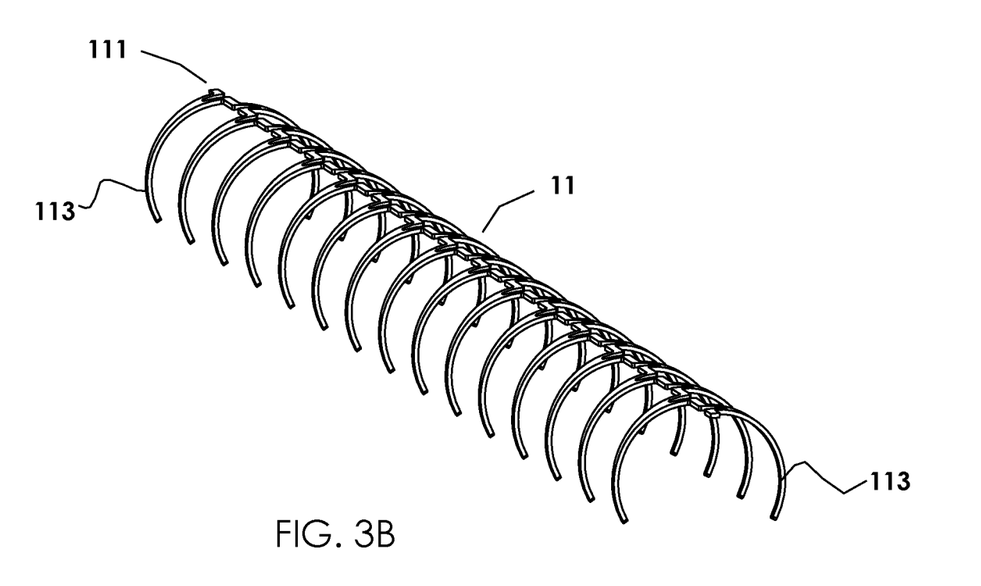
FIG. 3B is an isometric view illustrating the configuration of the compound stent after decomposition of one part of the compound stent.

As illustrated in FIG. 3B, over a given initial period after the implementation, the degradable stent (12) is eliminated by the body, e.g., absorbed in the body tissues, leaving the non-degradable stent in vessel (11). This initial period is defined by suitable choice of material and corresponding design of the stent portion (12), and is chosen to be somewhere in the range of 1 week to 6 months, and preferably in the range of 1 week to 3 months. In certain particularly preferred implementations, the initial period over which degradable stent portion (12) decomposes in in the range of 1 week to 1 month. In other particularly preferred implementations, this initial period is between 1 month and 3 months after completion of the initial procedure. As already mentioned, between 30 to 180 degrees of the perimeter is preferably not covered by the non-degradable stent (11) leaving a longitudinal swath free of struts along the vessel wall such that the inflammatory reaction does not occur along this swath. This helps to provide a lumen free of restenosis of a sufficient size to provide adequate blood flow. In contrast to the prior art, the swath is here formed after the initial healing period of the vessel wall.

Although described thus far primarily in relation to an implementation of the present invention in which the first stent portion is non-biodegradable, certain particularly preferred embodiments of the present invention employ a first stent portion which is also biodegradable, but with a longer period of persistence within the body, such that the first stent portion (11) continues to provide structural support within the vessel for a longer second time period, preferably extending at least 2 months, and more preferably at least 3 months, beyond the period in which the second stent portion (12) decomposes. In some cases, the differential between resorption times is achieved by use of two different biodegradable materials with different rates of breakdown within the body. Additionally, or alternatively, the structural design of the two stent portions (such as wall thickness, lateral dimensions and/or the presence of internal slots or apertures that change the surface to volume ratio) may differ so as to affect the resorption time for each.

In some cases, the two stent portions may be implemented of the same biodegradable material, and the aforementioned structural design features (such as wall thickness, lateral dimensions and/or the presence of internal slots or apertures that change the surface to volume ratio) are used to define the different rates of resorption. Particularly in the latter case, the first and second stent portions can be implemented as a single monolithic stent structure in which the device wall thickness etc. vary between the different regions of the device.

By way of one non-limiting example, FIGS. 7-13 illustrate a single-piece ("monolithic") stent construction in which part of the stent including a "backbone" structure has a wall thickness such that it forms the "first stent portion" which is biodegradable but has a relatively long period of persistence within the body, and a "second stent portion" is provided by thinner extending ribs which are more rapidly biodegradable. It should be noted that the change in wall thickness is not necessarily an abrupt change at a particular location, but may instead advantageously be a gradual transition or even a continuously variable parameter varying around the periphery of the stent structure. For example, according to one particularly preferred technique for forming a stent according to this aspect of the present invention, the stent may be cut out from a variable wall-thickness tube which is formed by machining, molding or otherwise forming a tube with an internal cylindrical surface having an axis which is slightly offset (eccentric) relative to an external cylindrical surface. The resulting structure is a tube with a thicker side, from which a continuous support structure extending along an axial length of the stent is formed, and a thinner side, from which the peripherally extending ribs are formed. Techniques for machining cylinders with an eccentric offset between axes of the internal and external cylindrical surfaces are known in the art.

In the case of a continuously variable wall thickness, the subdivision of the first and second stent portions may not be intuitively self-evident. However, the aforementioned design considerations preferably still apply and can be quantified in that, for example, an angular range of at least about 30° of the periphery of the expanded stent is preferably biodegraded during a first, shorter period, while sufficient support structure to support more than 180° of the periphery of the expanded stent (and blood vessel) preferably remains for a period that is at least 3 months longer than the first period. Where desired, the differential between the rates of breakdown of the different regions may be enhanced by providing the second stent portion with internal slots or apertures that increase the surface to volume ratio and hence accelerate breakdown of those regions.

Figure 10:
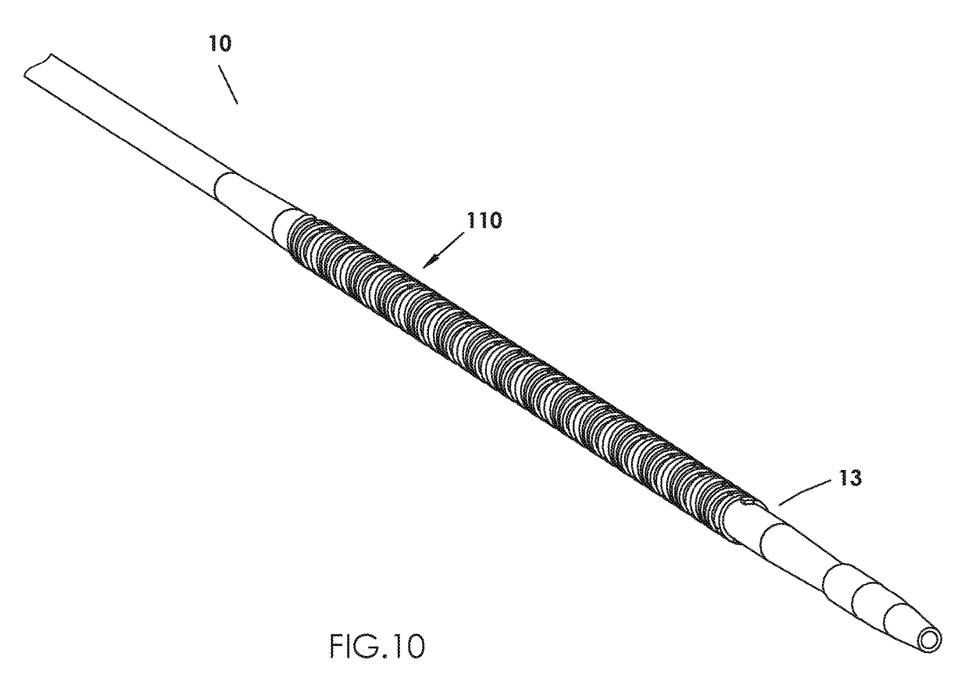
FIG. 10 is an isometric view illustrating the stent kit of FIG. 7 assembled in the compact insertion configuration, prior to deployment.
Figure 11A:
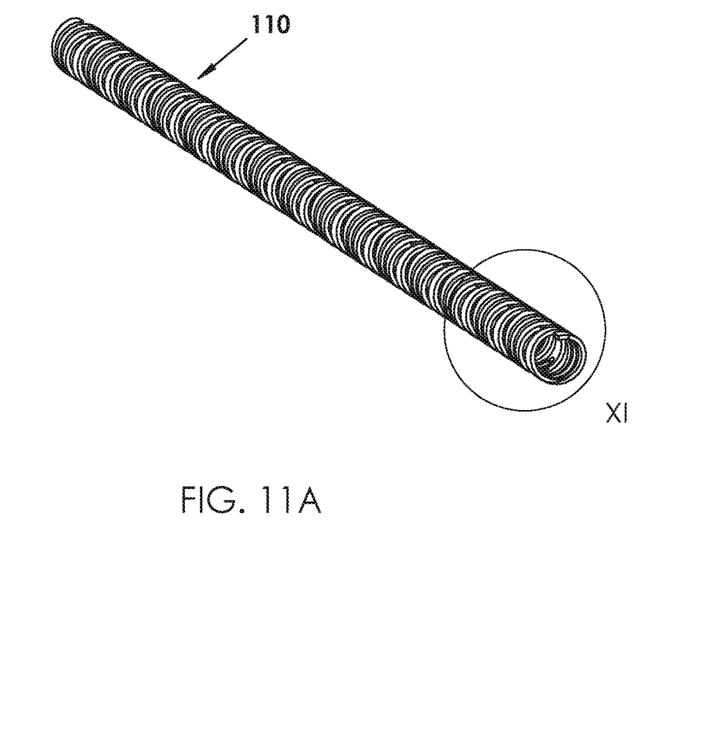
FIG. 11A is an isometric view similar to FIG. 10 but with the deployment balloon omitted.
Figure 11B:
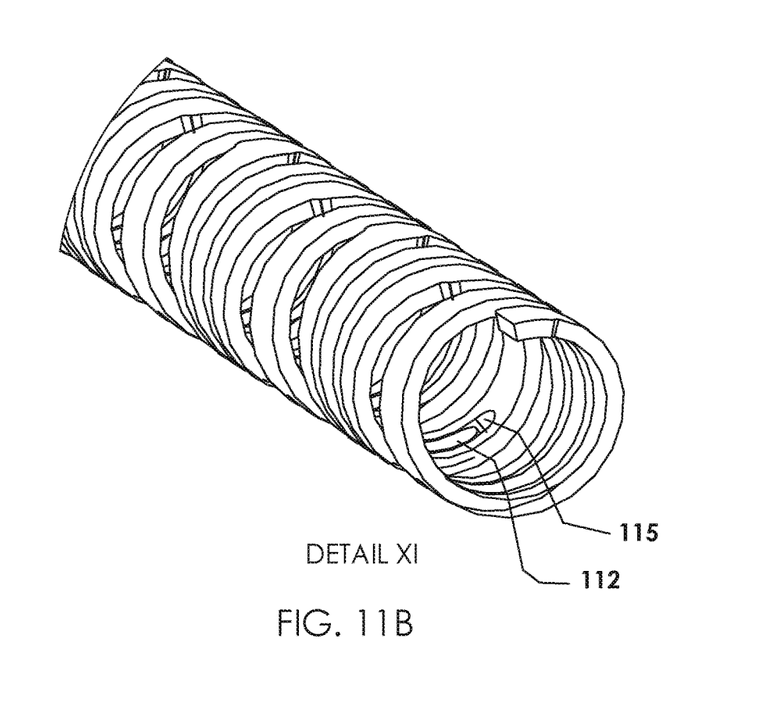
FIG. 11B is an enlarged view of the region of FIG. 11A designated by circle XI.
Figure 12:
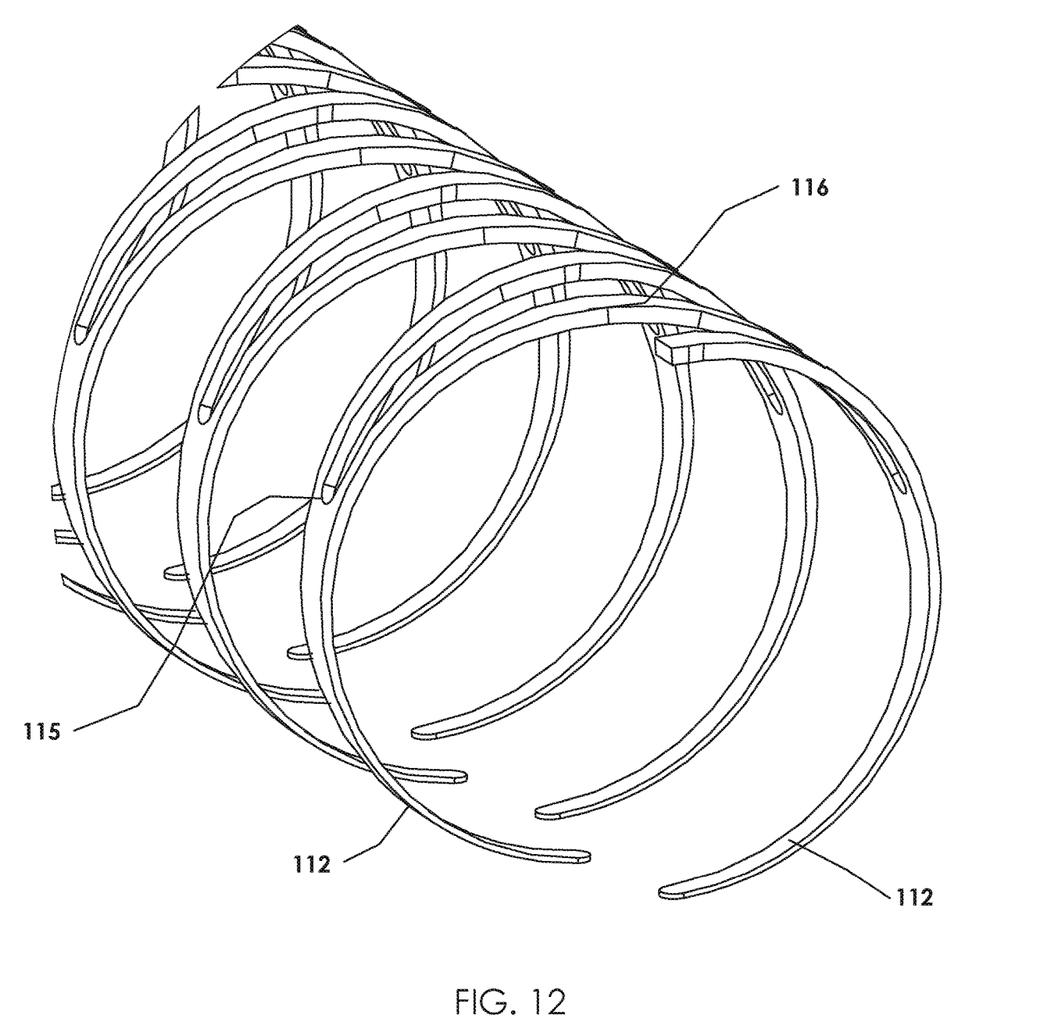
FIG. 12 is an enlarged view of the region of FIG. 9A designated by circle XII.
Figure 13:
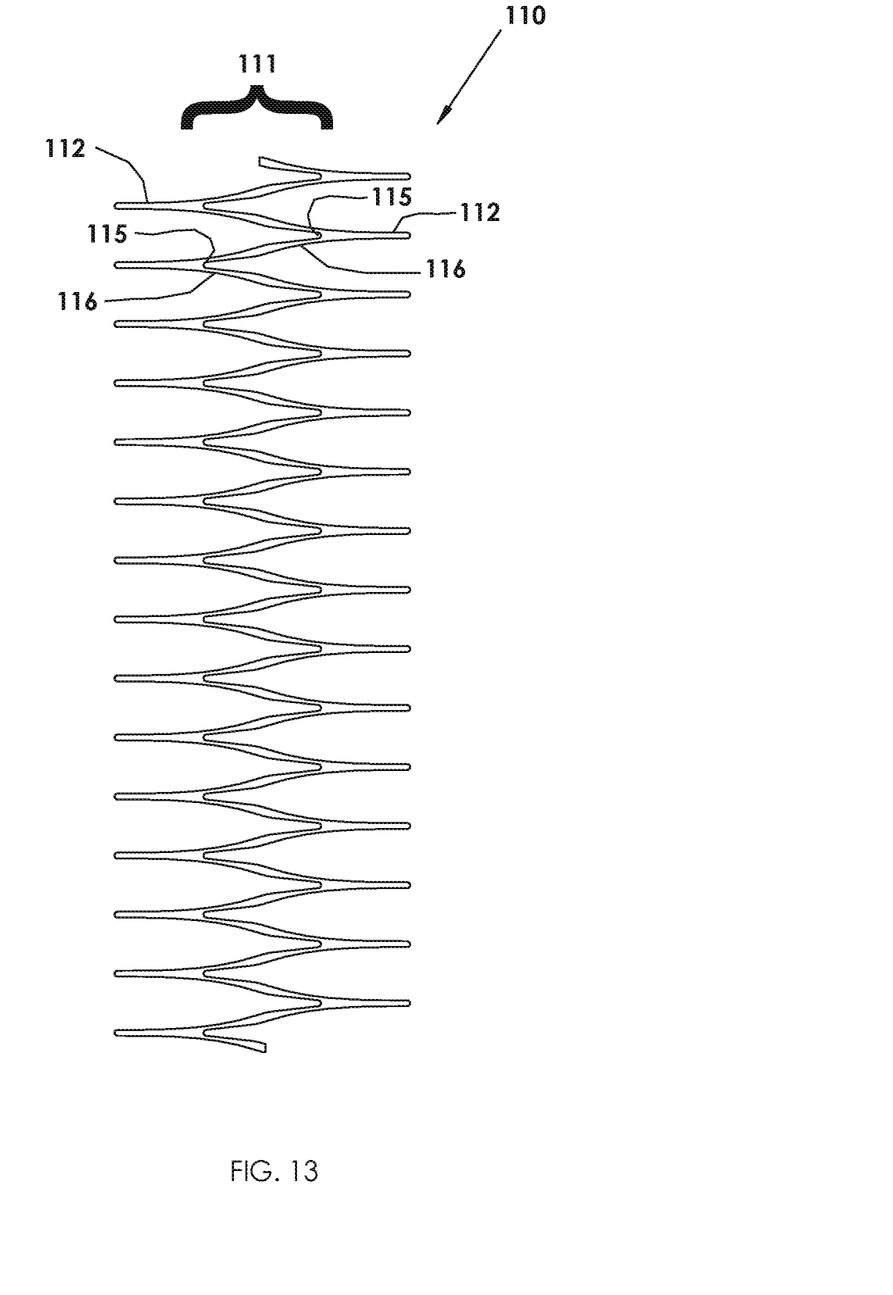
FIG. 13 is a plan view of the stent of FIG. 7 rolled out into a flattened form to better illustrate a preferred implementation of the stent geometry.

According to a further aspect of the present invention, useful in combination with the differential rate of resorption features but also of patentable significance in its own right, in order to provide a large range of proportional diameter increase in the case of a monolithic stent structure, the "backbone" (110) is preferably modified as shown (best seen in the schematic flattened version of FIG. 13) so as to form a zigzag pattern (i.e., alternating right- and left-angled segments (116) forming acute angled recesses (115) between them) with ribs (112) extending from the outside of some or all of the vertices of the to-and-fro pattern. The shape of the backbone defines recesses (115) into which the end of the corresponding rib can extend in the fully compacted state as closed around a balloon for insertion into the body (FIGS. 10, 11, 11A). In one particularly preferred implementation as illustrated here in FIG. 13, more than 20% and less than 40%, and most preferably roughly one third, of the extent of the stent width (or angular extent) is in the zigzag backbone, with the remaining width (or angular extent) divided between the ribs on each side, most preferably with roughly a third in the ribs projecting to each side. This facilitates closure of the stent as illustrated in FIGS. 10, 11, 11A to roughly one third of its deployed diameter while still maintaining full 360° support in its deployed state. The stent thus preferably achieves an expansion ration of at least 2.5:1, and most preferably at least 2.8:1.

Figure 4:
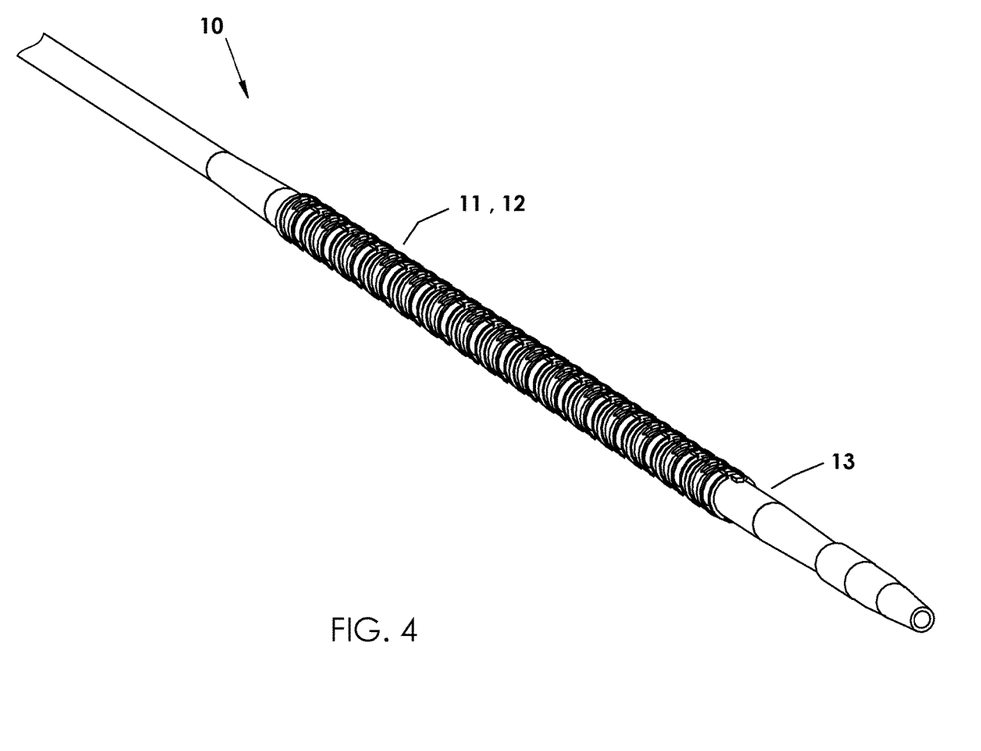
FIG. 4 is an isometric view illustrating the stent kit of FIG. 1 assembled in the compact insertion configuration, prior to deployment.

As illustrated in FIG. 4, prior to use, the stents (11, 12) are contracted on the angioplasty balloon (13) to provide a small crossing profile (diameter of the kit in its closed configuration). A typical crossing profile is of 0.9 mm to 1.3 mm, providing adequate space to be delivered through commercially available Guiding Catheters in the gauge size of 6 French.

Figure 5A:
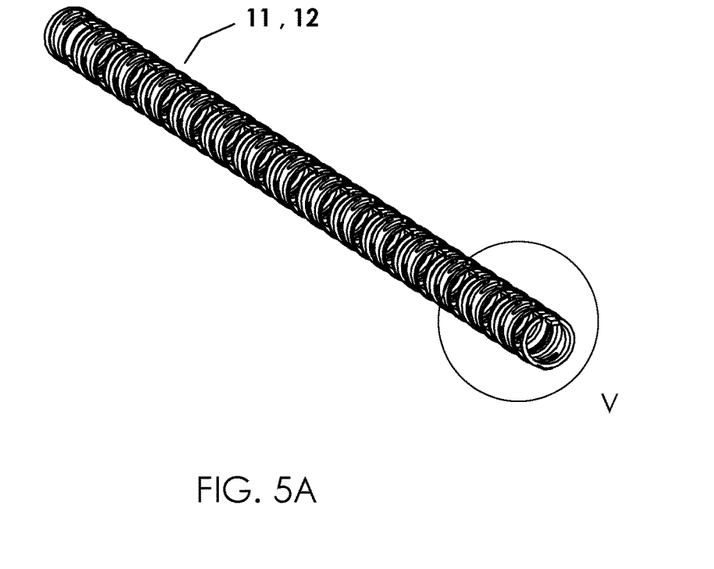
FIG. 5A is an isometric view similar to FIG. 4 but with the deployment balloon omitted.
Figure 5B:
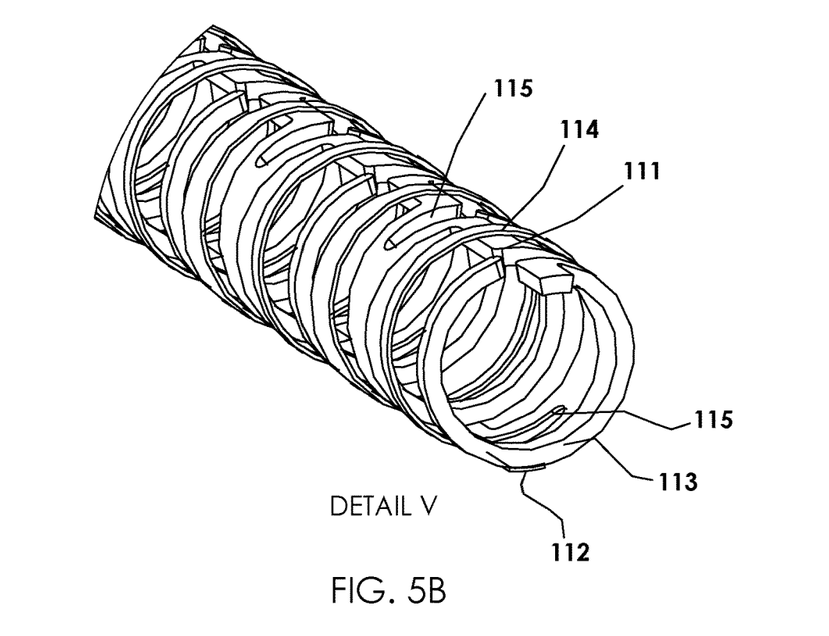
FIG. 5B is an enlarged view of the region of FIG. 5A designated by circle V.

As illustrated in FIG. 5A, which is a partial, enlarged view of part of the stent kit (10) in a contracted configuration as illustrated in FIG. 5, the degradable stent is preferably contracted over the durable stent such the backbone of each stent (111,112) is located 180 degrees opposite to the other. According to another particularly preferred but optional feature, the backbone of each stent is formed with V-shaped cutouts or recesses (115) at the root of each strut shaped to allow the tip of the strut to enter the cutout, thereby extending around slightly more than 360 total coverage in the compact state. (These V-shaped cutouts are essentially an embodiment of the zigzag backbone described above, but are typically less deep and typically have straight axial segments of backbone between them for the double stent configurations illustrated here.) With similar extending struts and cutouts in opposite directions from the backbone, the total angular coverage of each stent in the compact form is preferably over 540 degrees, and most preferably slightly over 720 degrees, with struts extending more than 360 degrees from one side and more than 360 degrees from the other. This preferably allows expansion of at least 3 times, and most preferably up to about 4 times, the compact configuration external diameter, while maintaining coverage of at least 180 degrees around the vessel internal wall in the expanded state.

It will be noted that the use of struts extending around more than 180 degrees inherently results in overlapping of the struts of each stent with the backbone of the other stent. Since the area of overlap is typically small, it has been found that frictional contact forces between the struts and backbones of the stents are also small, and do not interfere with deployment of the stents.

Figure 6:
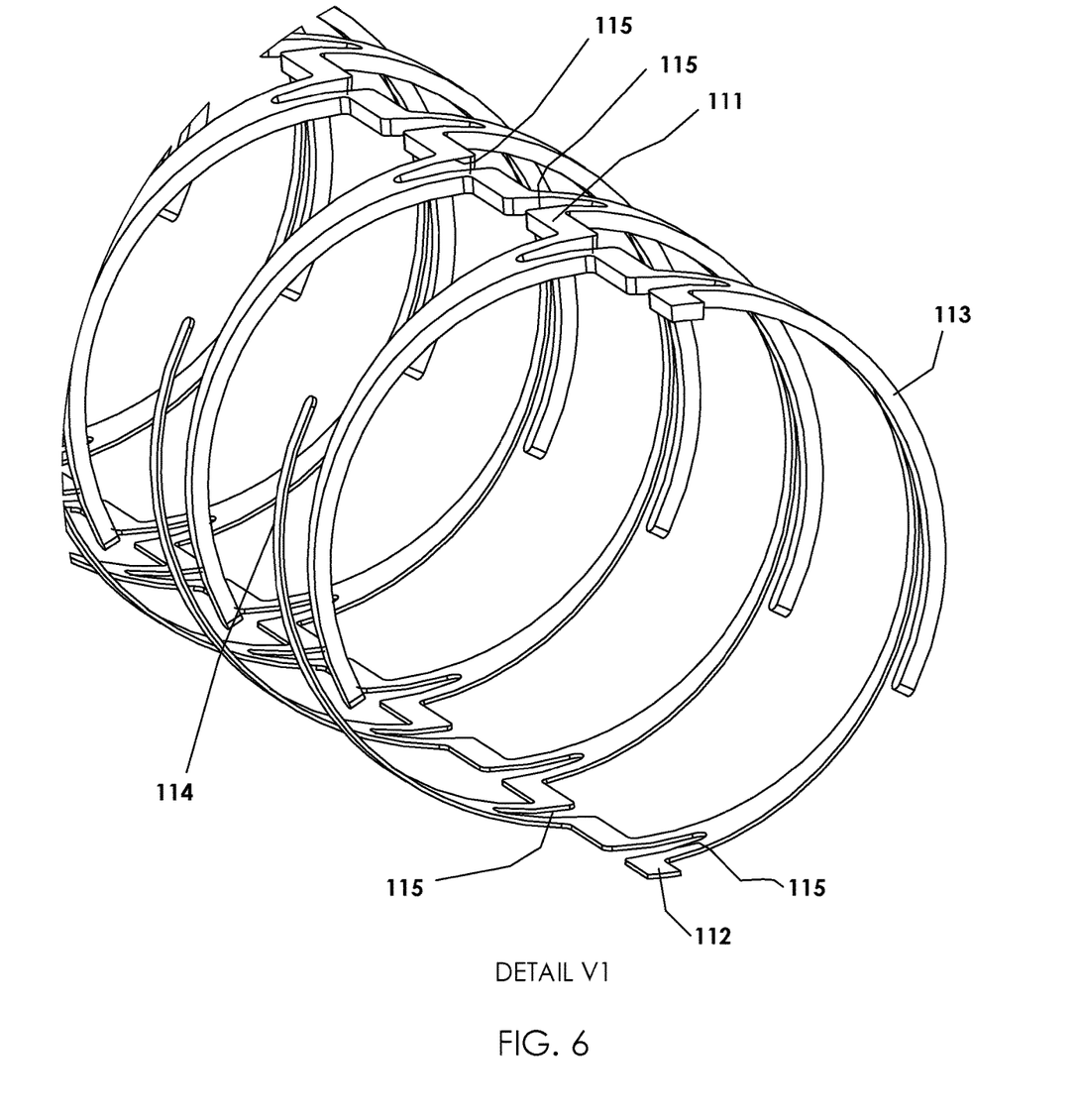
FIG. 6 is an enlarged view of the region of FIG. 3A designated by circle VI.
Figure 7:
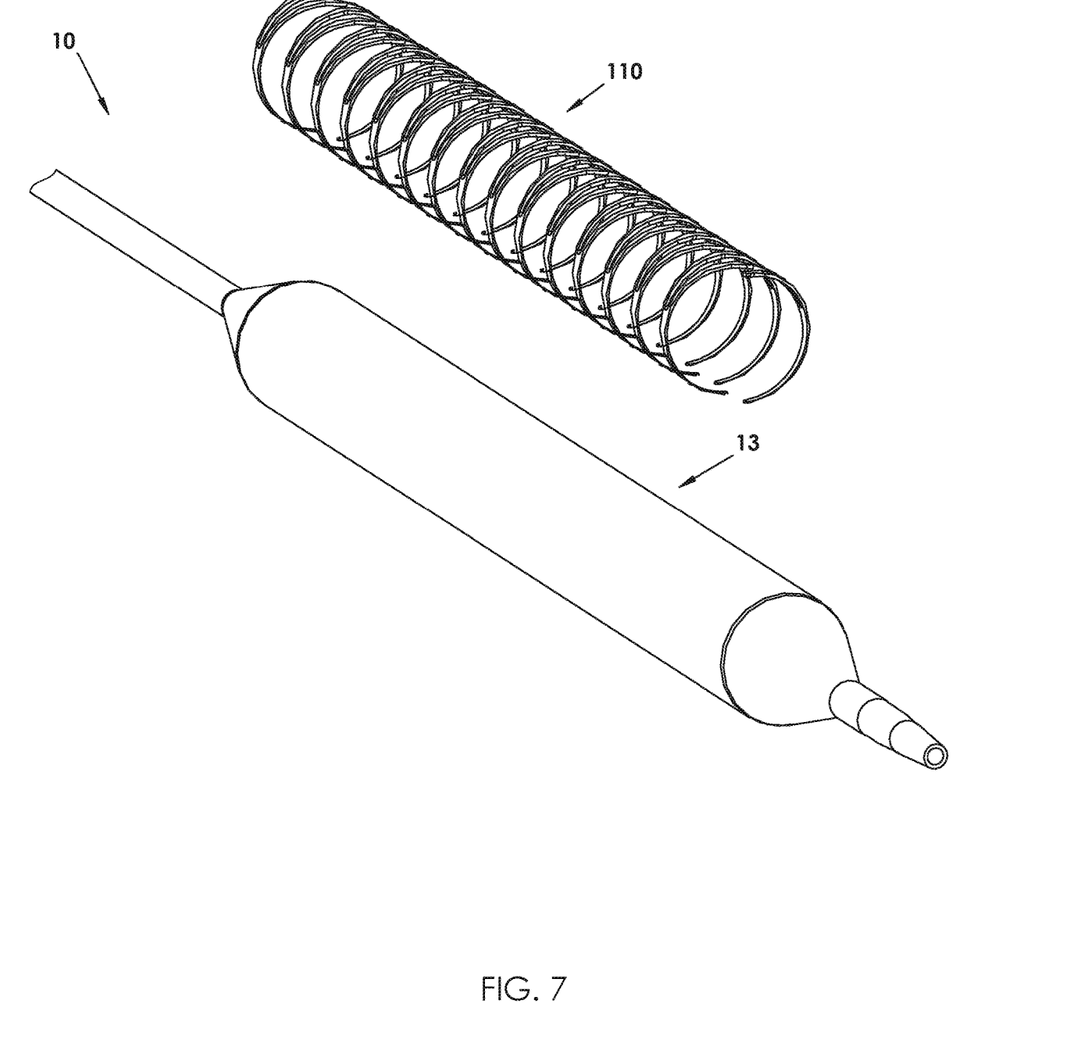
FIG. 7 is an isometric exploded view of a stent kit, constructed and operative according to the teachings of a further embodiment of the present invention, including a unitary progressively biodegradable stent and a deployment balloon.
Figure 8:
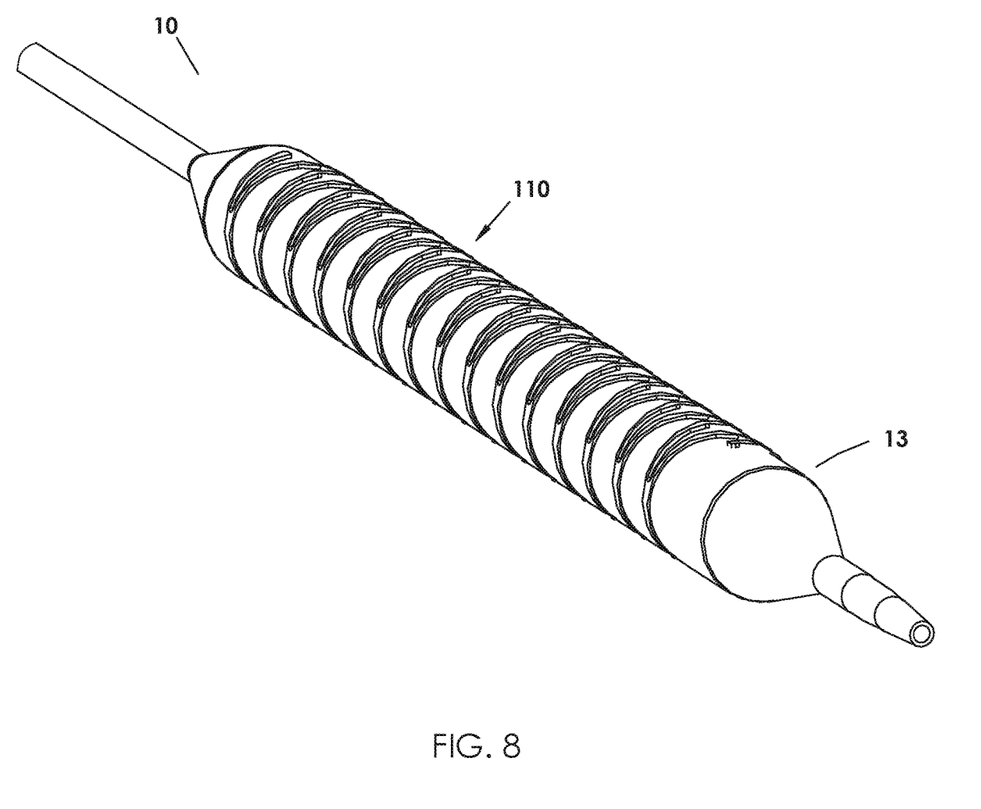
FIG. 8 is an isometric view of the stent kit of FIG. 7 assembled, illustrating the state of the kit after full inflation of the deployment balloon.
Figure 9A:
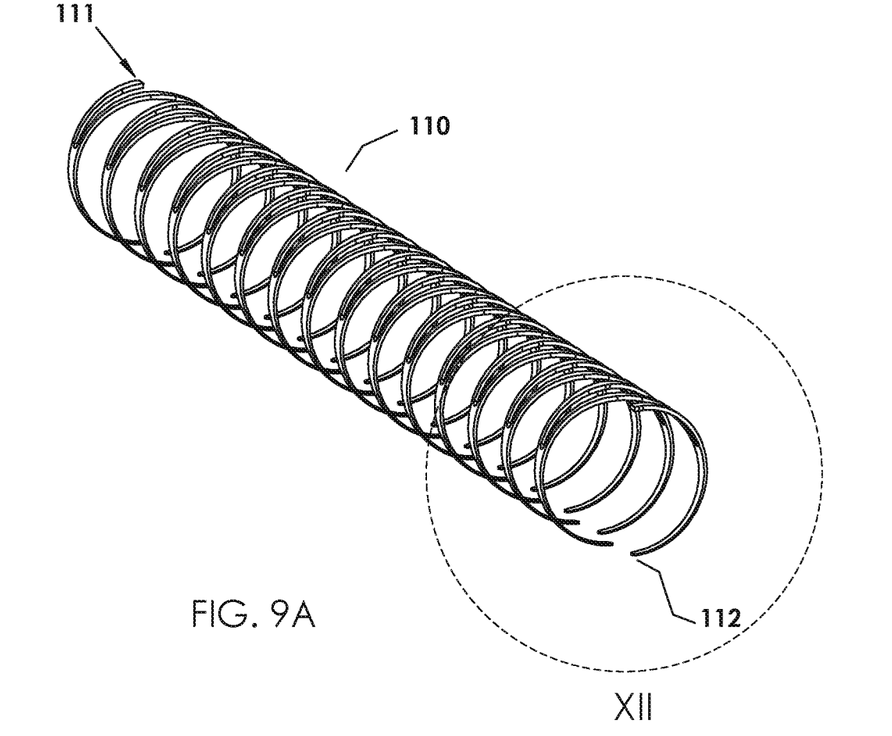
FIG. 9A is an isometric view illustrating the stent of FIG. 7 immediately after deflation and removal of the deployment balloon.
Figure 9B:
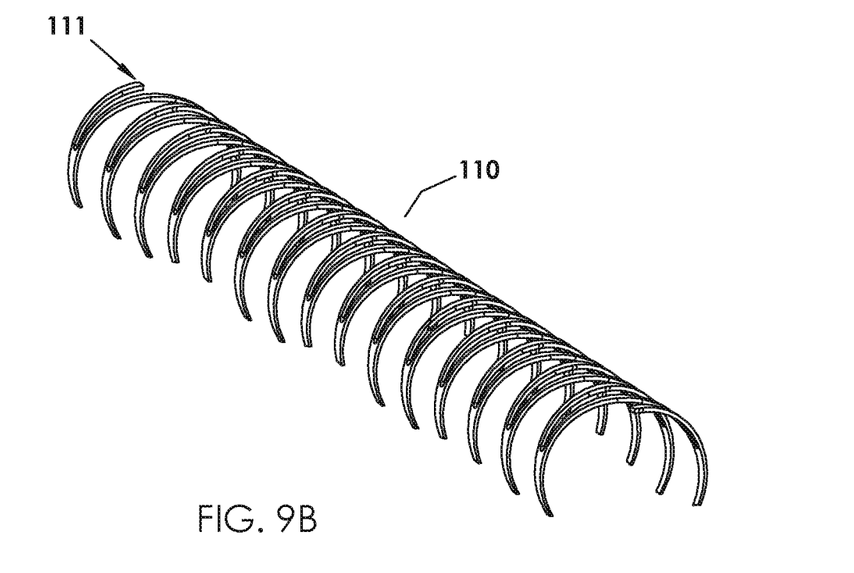
FIG. 9B is an isometric view similar to FIG. 9A illustrating the stent after decomposition of part of the stent.

When the stents are expanded to an open configuration as illustrated in FIG. 3A and in the enlarged view of FIG. 6A, the struts slide along an interior blood vessel wall in a direction of expansion of the blood vessel wall without leading edges of the peripheral surface contacting the interior blood vessel wall.

As illustrated in those figures, along the backbone of each stent (111, 121) the struts are arranged such that a group of close neighboring struts (arms) is to provide a support to the whole perimeter of the blood vessel.

This arrangement allow the stents kit to expand to up to four times its crossing profile (contracted diameter) hence with crossing profile of 1.2 mm the stent kit can be expanded to support a diameter of 4.8 mm. This contrasts favorably with commercial devices which, according to the literature, Percutaneous Transluminal Coronary Angioplasty (PTCA) procedures employ on average 3.0 mm diameter stents.

When the degradable stent (12) is degraded, a close group of struts remain and support more than 180 degrees of the perimeter of the vessel. Most preferably, even from the outset, the primary structural component of the compound stent device is the more durable portion (e.g., stent 11) whereas the degradable (or more rapidly degradable) portion (e.g., stent 12) serves primarily a short term function of preventing ingress of folds or flaps of tissue within stent (11) during an initial healing stage that typically takes up to a week. Onset of the degradation process for stent (12), and any associated change in mechanical properties of stent (12)

during that process, therefore have negligible impact on the overall mechanical performance of the compound stent.

Thus, certain embodiments of an apparatus and method of the present invention provide a stent (or a stent kit) that opens in a blood vessel in a manner that minimizes damage to arterial walls and reduces restenosis. The stent is a compound stent composed of a degradable stent portion and a non-degradable, or more slowly degradable, stent portion. Each stent portion is preferably configured so that, when expanded from a closed (low-diameter) state to an open (increased diameter) state, the peripheral surface of the stent slides along an interior surface of the blood vessel wall in a direction of expansion of the blood vessel wall, i.e., without any edge of the material advancing across a tissue surface. This is typically achieved by using a structure formed from an axial strip or "backbone" from which a plurality of peripheral struts (or "ribs" or "fingers") project, preferably bilaterally, forming partial hoops around the periphery of a cylindrical structure. The biodegradable stent portion and the non-biodegradable stent portion are preferably in counter-relation, with their backbones roughly opposite each other, and initially have their peripheral struts interposed, forming an interdigitated structure, with each stent portion encompassing close to 360 degrees around the small-diameter initial structure. When expanded, overlap is maintained so that the entirety of the vessel is initially supported. After break down of the biodegradable stent portion, the non-biodegradable stent portion remains alone, preferably leaving a swath of between 30 to 180 degrees of the perimeter free from contact with struts of the stent. In certain preferred embodiments, the degradable stent is used as delivery vehicles for anti-inflammatory drugs. In certain preferred cases, the arrangement of the stents allows the stent kit to expand to up to twice, and in some cases up to four times, its crossing profile (contracted diameter).

The above descriptions are intended only to serve as examples. Many other embodiments are possible within the scope of the present innovation as defined by the appended claims.

What is claimed is:

1. A compound stent device comprising:
   (a) a first stent portion; and
   (b) a second stent portion formed from a biodegradable material,
wherein said compound stent device is deformable from an initial compact state having a generally cylindrical profile with a first external diameter to an expanded state having a second external diameter greater than said first external diameter by a factor of at least two,
wherein, in the expanded state immediately after expansion, the first stent portion and the second stent portion cooperate to provide a first contact area of support for a length of a surrounding vessel around an entire internal periphery of the vessel, and wherein, in the expanded state after decomposition of the second stent portion, the first stent portion remains supporting more than half of periphery of the vessel while leaving a continuous swath of at least 30 degrees of the periphery of the vessel free from contact with the stent device, the first stent portion providing a second contact area of support for the length of the surrounding vessel, the second contact area being smaller than said first contact area by at least about 10 percent.

2. The compound stent device of claim 1, wherein the second contact area is smaller than said first contact area by at least about 40 percent.

3. The compound stent device of claim 1, wherein said first stent portion is formed from a non-biodegradable material.

4. The compound stent device of claim 1, wherein said first stent portion is formed from a biodegradable material that decomposes more slowly within the body than the biodegradable material of the second stent portion.

5. The compound stent device of claim 1, wherein said first stent portion is formed from the same biodegradable material as said second stent portion, and wherein said first stent portion is formed with a thicker structure than said second stent portion so that said first stent portion decomposes more slowly within the body than the second stent portion.

6. The compound stent device of claim 1, wherein said first stent portion is formed from a biodegradable material and is configured to decompose over a first time period, and wherein said second stent portion is configured to decompose over a second time period, said first time period being at least 2 months longer than said second time period.

7. The compound stent device of claim 6, wherein said second time period is between 1 week and 3 months.

8. The compound stent device of claim 1, wherein each of said first and second stent portions is formed with a backbone extending along a length of the stent portion and a plurality of struts projecting from each side of the backbone.

9. The compound stent device of claim 8, wherein said second stent portion is deployed with its backbone in opposing relation to the backbone of the first stent portion.

10. The compound stent device of claim 1, wherein the first stent portion is formed primarily from stainless steel.

11. The compound stent device of claim 1, wherein the second stent portion is formed primarily from magnesium.

12. The compound stent device of claim 1, wherein the second stent portion is configured to decompose within a blood vessel over a period of less than 3 months.

13. A compound stent device comprising:
   (a) a first stent portion formed from a non-biodegradable material; and
   (b) a second stent portion formed from a biodegradable material,
wherein said compound stent device is deformable from an initial compact state having a generally cylindrical profile with a first external diameter to an expanded state having a second external diameter greater than said first external diameter by a factor of at least two,
wherein, in the expanded state immediately after expansion, the first stent portion and the second stent portion cooperate to provide a first contact area of support for a length of a surrounding vessel around an entire internal periphery of the vessel, and wherein, in the expanded state after decomposition of the second stent portion, the first stent portion remains supporting more than half of the periphery of the vessel, while leaving a continuous swath of at least 30 degrees of the periphery of the vessel, free from contact with the stent device, the first stent portion providing a second contact area of support for the length of the surrounding vessel, the second contact area being smaller than said first contact area by at least about 10 percent.

14. The compound stent of claim 13, wherein the second contact area is smaller than said first contact area by at least about 40 percent.

* * * * *